(12) United States Patent
Miyoshi et al.

(10) Patent No.: US 6,980,853 B2
(45) Date of Patent: Dec. 27, 2005

(54) DEEP-VEIN THROMBOSIS DETERMINATION APPARATUS

(75) Inventors: Tsutomu Miyoshi, Tokyo (JP); Shuichi Izumi, Asaka (JP); Katsumi Takehara, Tokyo (JP); Yoshinori Fukuda, Akita (JP)

(73) Assignee: Tanita Corporation, Tokyo (JP)

( * ) Notice: Subject to any disclaimer, the term of this patent is extended or adjusted under 35 U.S.C. 154(b) by 326 days.

(21) Appl. No.: 10/369,508

(22) Filed: Feb. 21, 2003

(65) Prior Publication Data

US 2003/0163061 A1 Aug. 28, 2003

(30) Foreign Application Priority Data

Feb. 25, 2002 (JP) .............................. 2002-047840

(51) Int. Cl.[7] .............................................. A61B 5/05
(52) U.S. Cl. ................................................... 600/547
(58) Field of Search ............................... 600/547, 536, 600/513, 549

(56) References Cited

U.S. PATENT DOCUMENTS

| | | | |
|---|---|---|---|
| 3,871,359 A | 3/1975 | Pacela | |
| 4,314,563 A | 2/1982 | Wheeler | |
| 5,879,308 A * | 3/1999 | Rasanen | 600/536 |
| 5,991,654 A | 11/1999 | Tumey et al. | |
| 6,122,544 A * | 9/2000 | Organ | 600/547 |
| 2001/0044588 A1 | 11/2001 | Mault | |
| 2003/0199783 A1 * | 10/2003 | Bloom et al. | 600/549 |

OTHER PUBLICATIONS

Jindal G D et al: "Impedance plethysmography in Peripheral Vascular Occlusive Disorders" Proceedings of the Annual International Conference of the Engineering in Medicine and Biology Society, New Your, IEEE, US vol. 3 Conf. 9, Nov. 13, 1987, pp. 1611-1613.
Yongmin Kim et al: "Impedance Tomography and its Application in Deep Venous Thrombosis Detection", IEEE Engineering in Medicine and Biology Magazine, IEEE Inc. New York, US vol. 8, No. 1, Mar. 1, 1989, pp. 46-49.
European Search Report dated Jun. 27, 2003.

* cited by examiner

Primary Examiner—Max F. Hindenburg
Assistant Examiner—Brian Szmal
(74) Attorney, Agent, or Firm—McDermott Will & Emery LLP

(57) ABSTRACT

An apparatus is provided which allows a subject to determine by himself/herself whether or not he/she is apt to develop a deep-vein thrombosis in a region of a lower limb in a simple manner. A variation between the bioelectric impedance values measured respectively before and after a posture change is compared with a reference value. The posture change includes a bending and stretching exercise, a bending and stretching in knees in a seated position and a repeating of standing-up and sitting-down motion. Alternatively, a blood storage capacity of the lower limb region may be estimated from a gradient of bioelectric impedance represented by a variation thereof per unit time to determine whether or not the subject is apt to develop deep-vein thrombosis in the lower limb region.

4 Claims, 7 Drawing Sheets

DEEP-VEIN THROMBOSIS DETERMINATION APPARATUS

BACKGROUND OF THE INVENTION

1. Field of the Invention

The present invention relates to an apparatus for determining whether or not a subject person has a status or constitution apt to develop deep-vein thrombosis occurring in a region of lower limb if he/she remains seated on a chair for many hours.

2. Prior Art

Recent years, a symptom called "economy-class syndrome" has been emphasized. This symptom may cause a blood circulation disorder such as thrombosis resultant from sitting on a narrow seat in an airplane for many hours without moving legs. In specific, a pumping action by muscle contraction around blood vessels would be no more effective, which could bring a body into a condition where the blood would be more likely to be clotted in a vein due to a jam (stagnation) of blood. Thus developed clot is referred to as a thrombus. It has been said that in a case where the thrombus has been produced particularly in a vein located in a deep region of a thigh (deep-vein thrombus), if the subject person in that condition starts to walk, then the thrombus will ride on the blood flow, which could block a vessel in a lung, developing a pulmonary thromboembolism and resulting in death of the subject person in the worst case. This symptom would not be developed exclusively in the airplane but the report says that there are also some cases of this symptom developed in a long time car driving or working in a seated position.

The symptom developed particularly in a region of lower limb is referred to as a deep-vein thrombosis in medical language, and it is considered that in one precautionary measure, moving muscles moderately to stimulate the blood circulation in legs can prevent this symptom but moving only an upper body without moving legs would not bring any effect. This means that the development of the deep-vein thrombosis can be prevented by moving legs to a moderate degree.

As pointed above, the deep-vein thrombosis in the lower limb region is considered to be a serious symptom involving in human lives, but there has been so far no effective method and/or apparatus provided for giving an objective determination whether or not the subject has the status that may easily develop this thrombosis with only the determination given conventionally according to a doctor's subjective point of view.

Further, in diagnosing on the pulmonary thromboembolism resultant from the development of the deep-vein thrombosis in the lower limb region, a blood test, an angiography in a lower limb, a blood flow measurement, a chest X-ray, an electrocardiography and so on have been used to determine an oxygen partial pressure and/or a carbon dioxide partial pressure. An engineer dedicated in operating those units for testing and/or measuring these items or values is required, which has made it not-easy to obtain the diagnosis.

SUMMARY OF THE INVENTION

The present invention has been made in the light of the problems as clarified above, and an object thereof is to provide an apparatus enabling a simple recognition personally by a subject on whether or not the subject has a status apt to develop the deep-vein thrombosis, thereby avoiding the development of the deep-vein thrombosis in the lower limb region, which otherwise might lead to the pulmonary thromboembolism.

According to an aspect of the present invention, there is provided a deep-vein thrombosis determination apparatus comprising a plurality of electrodes, a current supply unit, a voltage measuring unit, an arithmetic operation unit, a storage unit, a determination unit and an informing unit, wherein said plurality of electrodes includes current supply electrodes and voltage measuring electrodes to be installed in contact with both feet of a subject's body, said current supply unit supplies an alternating current between said current supply electrodes, said voltage measuring unit measures a voltage between said voltage measuring electrodes, said arithmetic operation unit calculates a bioelectric impedance value from the supplied alternating current and the measured voltage, said storage unit stores a reference value, said determination unit evaluates a status relative to a deep-vein thrombosis in a region of lower limb based on a comparison between the calculated bioelectric impedance value and the stored reference value, and said informing unit informs the subject of a determined result, thereby enabling the subject to have a knowledge in a simple manner on whether or not he/she has the status apt to develop the deep-vein thrombosis in the lower limb region.

Further, according to an embodiment of a deep-vein thrombosis determination apparatus of the present invention, said arithmetic operation unit uses said plurality of electrodes, said current supply unit and said voltage measuring unit to execute an arithmetic operation on the bioelectric impedance value at least two times, one before and one after a change in a subject's body orientation, and to execute an arithmetic operation on a variation of the measured bioelectric impedance values; and said determination unit evaluates the status relative to the deep-vein thrombosis in a region of lower limb based on a comparison between the calculated variation of the bioelectric impedance value and the reference value stored in the storage means, thereby enabling an accurate determination by acquiring a movement of blood flow by the muscular pumping action of the subject.

Still further, according to an alternative embodiment of a deep-vein thrombosis determination apparatus of the present invention, said arithmetic operation unit uses said plurality of electrodes, said current supply unit and said voltage measuring unit to execute an arithmetic operation on a gradient of bioelectric impedance represented by a variation thereof per unit time from a time period for which a subject remains in a certain body orientation and a variation of the bioelectric impedance value during said time period of that certain body orientation; and said determination unit evaluates the status relative to the deep-vein thrombosis in a region of lower limb based on a comparison between the calculated gradient of bioelectric impedance represented by the variation thereof per unit time and the reference value stored in the storage unit, thereby providing a determination based on a movement and storage capacity of blood in the region of lower limb of the subject.

Yet further, according to still alternative embodiment of a deep-vein thrombosis determination apparatus of the present invention, since said apparatus further comprises an input device for inputting a set of personal information relating to a physical body of a subject, wherein said storage unit stores a plurality of reference values each corresponding to different set of said personal information, and said determination unit selects a certain reference value among those reference values having stored in the storage unit so as to be used in a determination based on said input set of physical information of the subject, therefore the status of the subject can be evaluated more accurately.

Yet further, according to still alternative embodiment of a deep-vein thrombosis determination apparatus of the present invention, since said apparatus further comprises an input device for inputting a relevance degree of subject to respective factors involved in a deep-vein thrombosis in a region of lower limb, wherein said determination unit modifies the reference value to be used in a determination based on the input relevance degree of subject, therefore the status of the subject can be evaluated more accurately.

Yet further, according to still alternative embodiment of a deep-vein thrombosis determination apparatus of the present invention, since in said apparatus, said informing unit further provides an advice relating to a prevention of deep-vein thrombosis in a region of lower limb, therefore the subject can be provided with a knowledge of prevention method.

DESCRIPTION OF PREFERRED
EMBODIMENTS

It is thought that a deep-vein thrombosis tends to be developed with those having such status in which blood is apt to be stored within veins located in a deep region of lower limb. It is also believed that those exhibiting a smaller variation in quantity of blood within the vein located in the deep region of lower limb by a change in a body orientation has a status apt to develop the deep-vein thrombosis, and based on this thought, in a determination apparatus of the present invention, a subject is instructed to change his/her body orientation from one to another so as to apply a load to muscles in the lower limb region. This is because the blood stored in the vein located in the deep region of lower limb can be circulated entirely within the body with the aid of the muscular pumping action effected by changing the posture of the subject. Measuring of a difference in bioelectric impedance value between before and after this change of posture can help judge a movement of a body fluid (blood) within the body.

To change the posture of the subject, those motions including a bending and stretching exercise, a bending and stretching of knees in a seated position, and a repeating action of standing-up and sitting-down may be considered useful, and then a variation in bioelectric impedance values measured respectively before and after the change in the posture by those motions may be compared to a reference value, thereby determining whether or not the subject has the status apt to develop the deep-vein thrombosis in the lower limb region.

Figure 1:
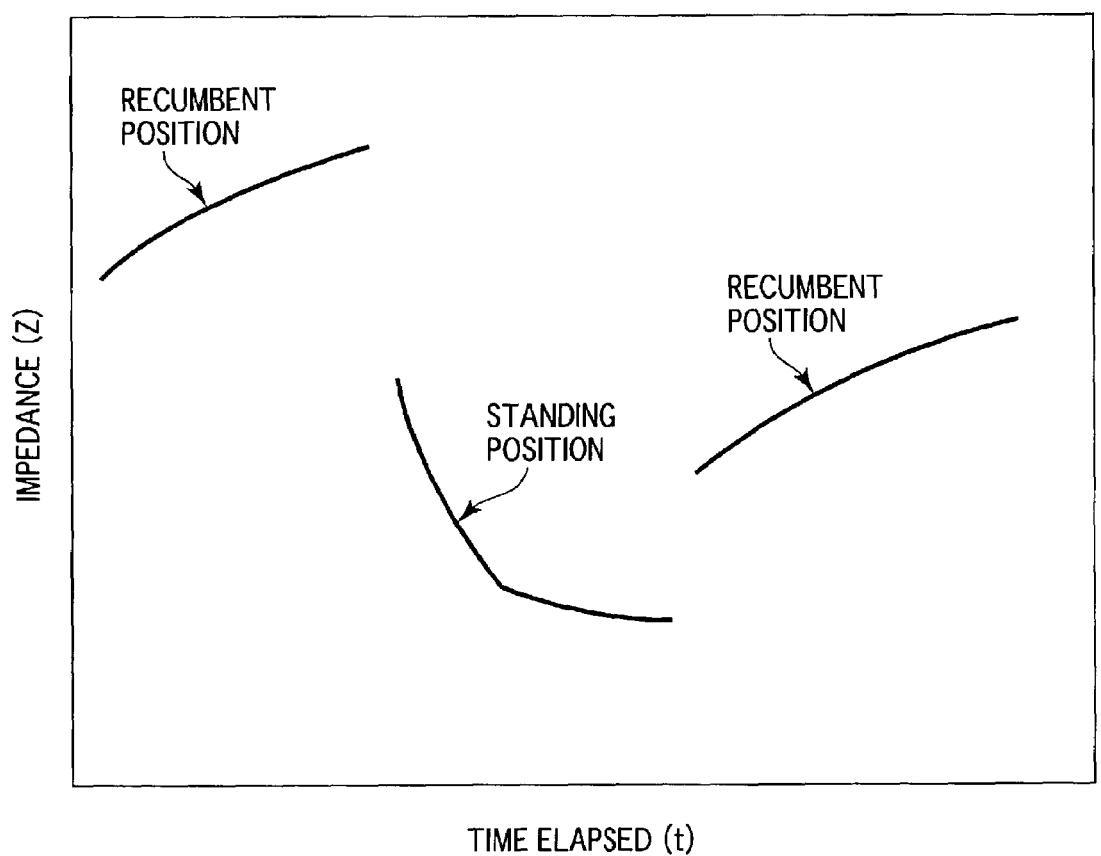
FIG. 1 is a graph showing a feature of variation in bioelectric impedance during a time period for each different body orientation.

FIG. 1 is a graph showing a feature of variation in bioelectric impedance obtained from a result of test in which the inventors of the present invention have actually measured the bioelectric impedance between one and the other feet over a certain time period in association with the posture change for a plurality of subjects.

In the above test of measurements, the motion of the subject was first constrained so as not to move their lower limbs while keeping a recumbent position for a predetermined time period (about 20 minutes), then the subject was instructed to bring his/her body orientation into a standing position and to remain in standing condition (for about 15 minutes), and the subject was once again brought into the recumbent position and constrained not to move his/her lower limbs (for about 20 minutes).

As can be seen from the graph, since the subject has been in the standing or the seated position before the first recumbent position, the body fluid such as blood and lymph has been stored much in the region of lower limbs, and once the subject takes the recumbent position, the body fluid is no more stored in a particular region of the body but dispersed across the entire body. As regards the lower limb region, the quantity of the body fluid has been decreased and thereby the bioelectric impedance value is observed to rise gradually.

Subsequently, when the subject changes the body orientation into the standing position, the blood and/or lymph starts to be circulated by the motion of the lower limb muscles (the muscular pumping action) upon standing up, while the blood and/or the lymph which have been dispersed across the entire body start to be stored in the region of lower limbs due to the standing position, thus making the bioelectric impedance value dropped at a stretch. Thereafter, as the quantity of body fluid stored in the lower limbs is getting higher, the bioelectric impedance value continues to decrease, but as approaching to an allowable level of the body fluid to be stored in the lower limbs, the bioelectric impedance value between both feet exhibits a gradual dropping. It is considered that this gradient of bioelectric impedance may be changed in dependence on a difference in the capacity in the region of lower limb of the subject for storing the body fluid, such as the blood and/or lymph, wherein a person allowing more quantity of body fluid to be stored in the lower limb region has a greater gradient, while a person allowing less quantity of body fluid to be stored in the lower limb has a smaller gradient.

After that, when the subject is constrained again so as not to move the lower limbs in the recumbent position, the blood and/or lymph having stored in the lower limbs start to be dispersed and the quantity of body fluid in the region of lower limbs is decreased, thereby increasing the bioelectric impedance value gradually.

From the fact described above, it is considered that the variation in bioelectric impedance value is induced in the event of the change from one certain posture to another posture, and that the gradient or the variation degree of the bioelectric impedance between different postures is involved with the capacity of the subject for storing the blood and/or the lymph in the lower limbs and/or whether or not the body fluid is smoothly transferred during changing postures, for example, from the standing position to the recumbent position. In this point, a person more apt to transfer and store a large quantity of body fluid in the region of lower limbs may have the bioelectric impedance value that could continue to drop rapidly as he/she changes the postures from the recumbent position to the standing position. That is, the person having a higher ability for transferring the body fluid into the region of lower limbs and a higher capacity for storing the blood in the region of lower limbs is associated with more chances of the blood stagnancy and longer storing period, and such a person can be considered to have the status allowing the blood to be stored more easily in the region of lower limbs.

Accordingly, a determination apparatus of the present invention can determine whether or not the subject has the status apt to develop the lower limb deep-vein thrombosis also from the gradient of bioelectric impedance.

Further, a determination apparatus of the present invention takes into account an age and/or a sex of the subject and/or a relevance degree of subject to some factors considered to be involved in a deep-vein thrombosis in order to make a determination on whether or not the subject has the status apt to develop the deep-vein thrombosis.

Still further, a determination apparatus of the present invention can provide an advice on a method for preventing the deep-vein thrombosis.

DESCRIPTION OF SOME EXAMPLES

Figure 2:
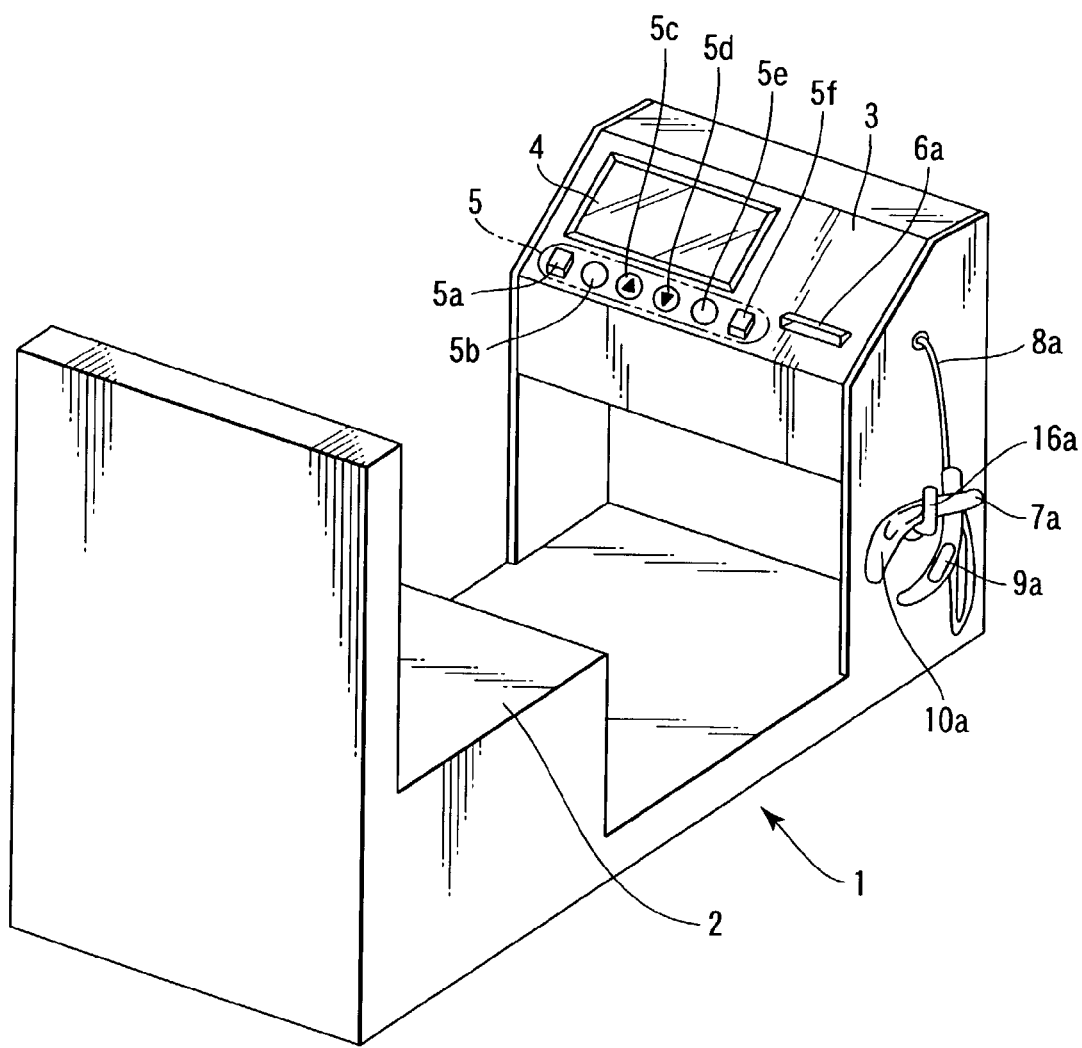
FIG. 2 is a schematic perspective view of a determination apparatus according to a first embodiment of the present invention.

One embodiment of the present invention will now be described with reference to the attached drawings. FIG. 2 shows a schematic perspective view of deep-vein thrombosis determination apparatus in the lower limb region.

This determination apparatus 1 is built as a single body incorporated with a seating section 2 on which a subject may sit, and it includes a control box 3 disposed in the front section thereof.

The control box 3 includes a display 4 serving as an informing means for indicating various sets of information, such as measured results and advices, and an input device 5 serving as an input means comprising a plurality of switches, which is disposed below the display 4. The input device 5 comprises a power switch 5a, a set switch 5b, an up switch 5c, a down switch 5d, a decision/end switch 5e and a print switch 5f, which are arranged in order from left to right.

The control box 3 further includes a paper ejector 6a for ejecting a printed sheet of paper on which the information such as results and advices have been printed by the printer 6, though not shown.

Further, measuring clips 7a, 7b comprising electrodes for measuring the bioelectric impedance are connected to the left and the right side faces of the control box 3 via cords 8a, 8b respectively, and those clips 7a, 7b are to be attached to ankles of the subject.

In the inner side of the measuring clip 7a for the right foot are installed a current supply electrode 9a and a voltage measuring electrode 10a. Although not shown in the drawing, the measuring clip 7b for the left foot has a similar configuration.

The side face of the control box 3 is further provided with a clip holder on which the measuring clip is hung while it is not used, and FIG. 2 shows a state of the measuring clip 7a hung on the clip holder 16a.

Figure 3:
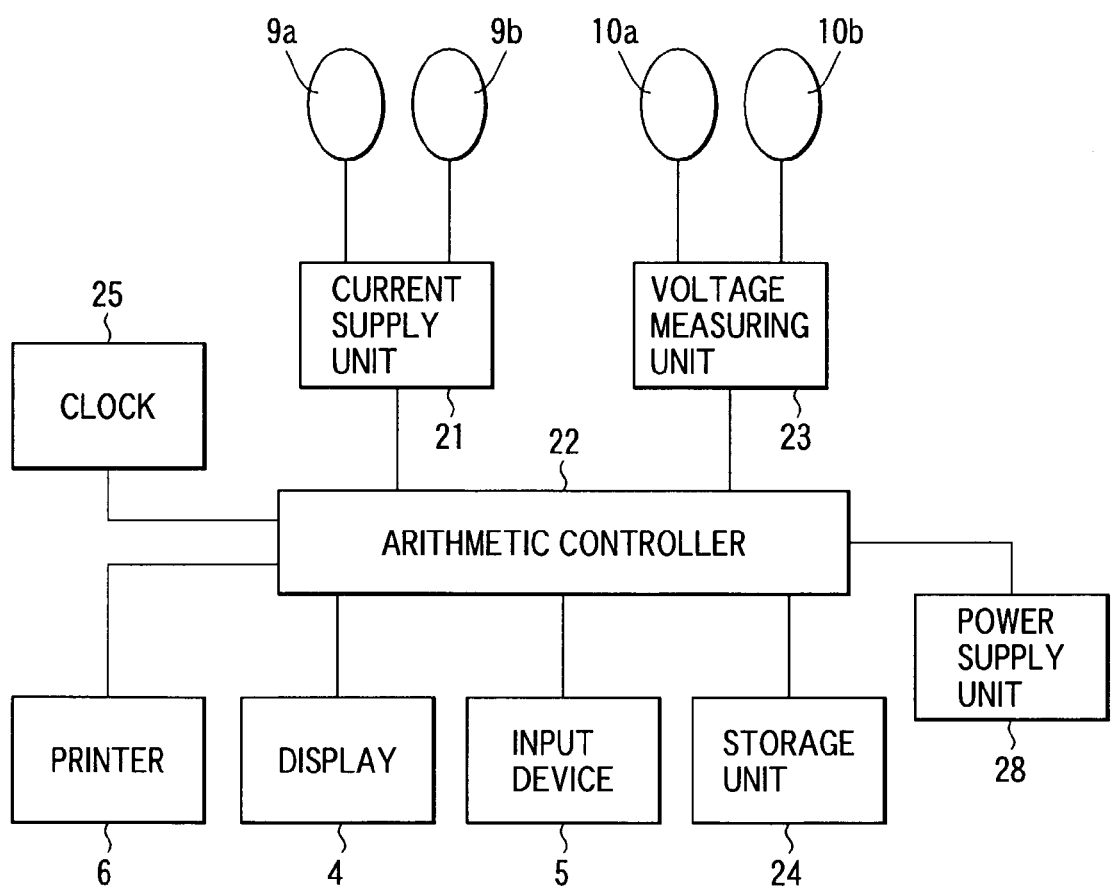
FIG. 3 is a block diagram employed in the determination apparatus according to the first embodiment of the present invention.

FIG. 3 is a block diagram of the determination apparatus 1.

The current supply electrodes 9a, 9b are connected to a current supply unit 21 serving as a current supply means, and this current supply unit 21 is connected to an arithmetic controller 22 for executing a variety of operations and controls of respective devices. Further, the voltage measuring electrodes 10a, 10b are connected to a voltage measuring unit 23 serving as a voltage measuring means, and this voltage measuring unit 23 is also connected to the arithmetic controller 22.

The arithmetic controller 22 is further connected with the display 4 for indicating results, the input device 5 comprising a plurality of switches, the printer 6 for printing the results, a storage unit 24 serving as a storage means for storing various information such as a set of input data and measured bioelectric impedance values, and a clock 25 for clocking a predetermined time period.

Besides, a power supply unit 28 functions to supply electric power to the arithmetic controller 22 and each of other units and devices.

Figure 4:
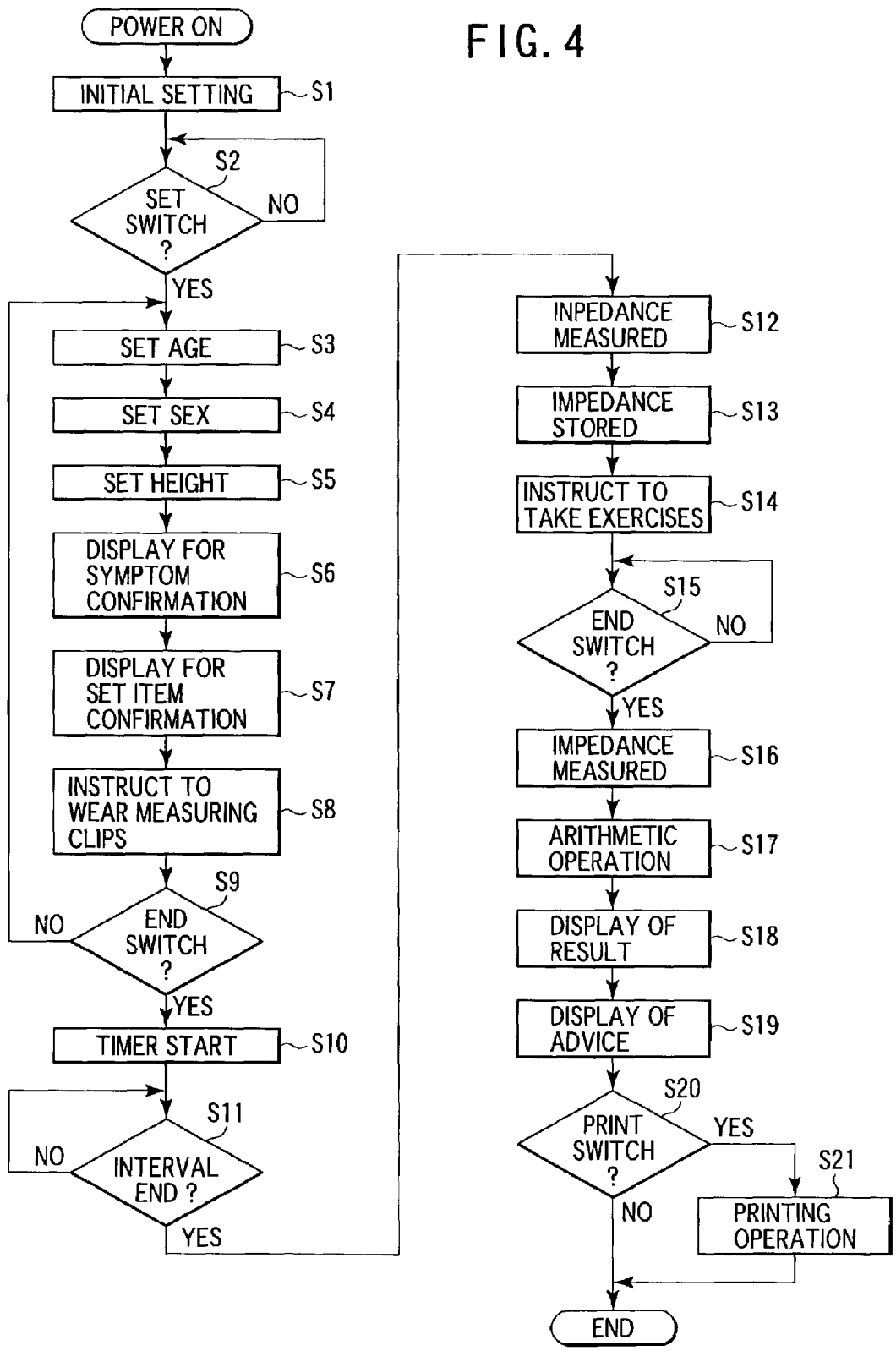
FIG. 4 is an operation flow chart for the determination apparatus according to the first embodiment of the present invention.

Now turning to FIG. 4, a flow of operations in the determination apparatus 1 of the present invention will be described.

First of all, the power switch 5a is pressed, and respective units and devices such as the arithmetic controller 22 and the storage unit 24 in the determination apparatus 1 are initialized (Step S1) into a state ready for determining whether or not the set switch 5b for setting a personal physical information is pressed (Step S2). The respective units and devices would be held in the stand-by states until the set switch 5b is pressed and accordingly the display 4 continues to indicate an initial screen thereon.

When the set switch 5b is pressed, it is determined YES in Step S2 and the process moves to Step S3 to S5 to receive an input of the personal information for a subject. In this embodiment, the up switch 5c and/or the down switch 5d are pressed so as to change an initial value or information indicated in the display 4 in order to give a correct age, sex and body height of the subject, and then the decision/end switch 5e is pressed to confirm the set value or information (Step S3 to S5).

Next in Step S6, an input operation is executed on whether or not the subject has any relevance factors considered to stimulate the development of the deep-vein thrombosis in the lower limb region.

In this embodiment, the following items are indicated as specific items to be confirmed for the factors (Step S6);

Does the subject have any chronic diseases, such as diabetes, hyperlipemia and hypertension?

Does the subject have any malignant tumor such as cancer?

Has the subject taken any abdominal or intrapelvic surgical treatment or had any bone fracture recently?

Is the subject now taking any pills or in pregnancy or just after giving birth?

If there are any relevant items among those, input a counted number of those relevant items.

After finishing of the setting of the number of relevant items, all of the items which have been set in the steps S3 through S6 are indicated in the display 4 (Step S7).

Then, an instruction is indicated on the display 4 to guide the subject to put on the measuring clips 7a, 7b around both feet (Step S8).

Figure 5:
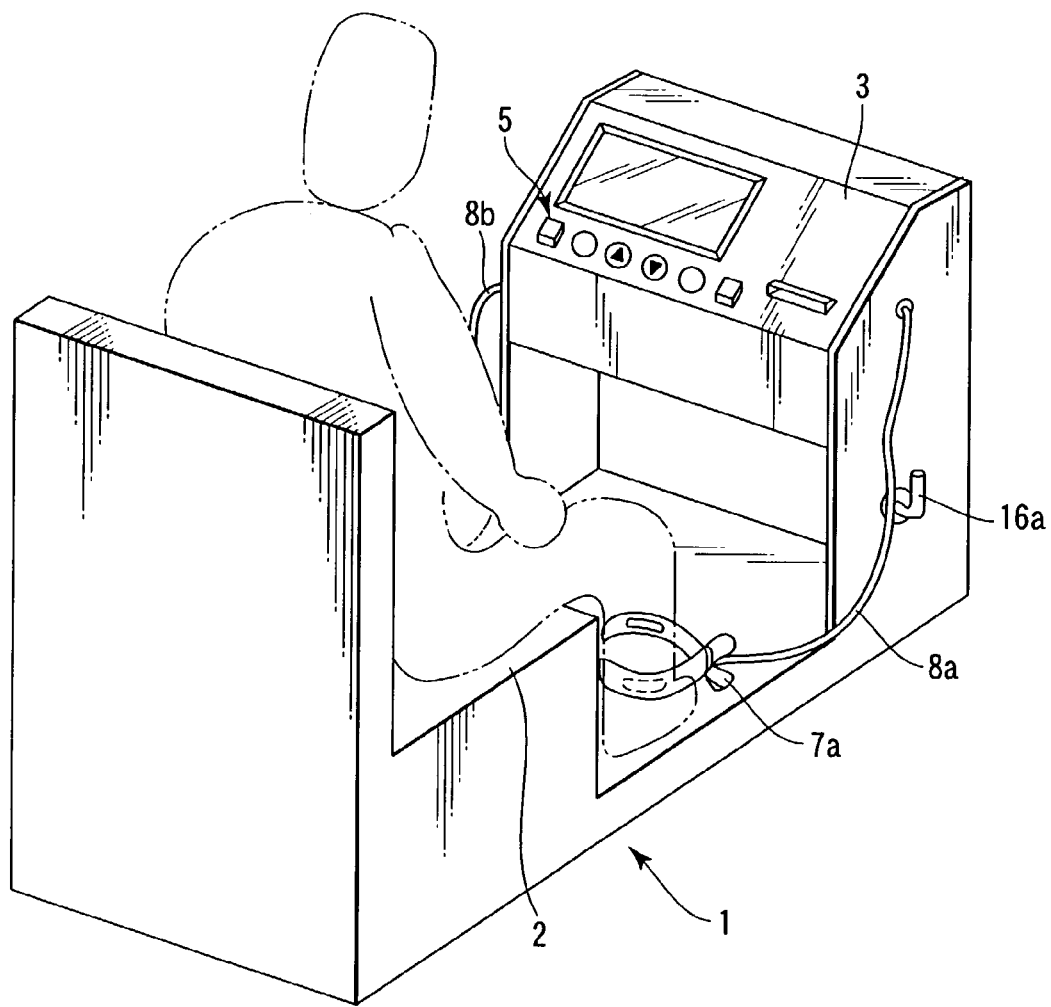
FIG. 5 is a schematic perspective view illustrating a measuring mode of the determination apparatus according to the first embodiment of the present invention.

The subject puts on the measuring clips 7a, 7b, on his/her both feet in rather upper locations of the ankles, respectively. FIG. 5 shows the measuring clips 7a, 7b having put on the feet of the subject.

After completing the fitting of the measuring clips 7a, 7b, the subject presses the decision/end switch 5e (Step S9).

In this stage, the display 4 indicates "Stay at rest with your legs unmoved and remain seated" and the clock 25 is activated to start clocking a predetermined time period (Step S10).

This may bring the subject into a condition where the blood is forced to be stored in legs by limiting the motions of legs. A few minutes of constraint should be necessary to achieve this, and in this embodiment a five-minute-interval is provided.

Accordingly, the clock 25 clocks for 5 minutes, and after this five-minute-interval has elapsed (Step S11), a measurement of the bioelectric impedance between both feet of the subject is started.

An alternating current from the current supply unit 21 is supplied into the body of the subject via the current supply electrodes 9a, 9b, and a voltage between the voltage measuring electrodes 10a, 10b is measured by the voltage measuring unit 23, while the arithmetic controller 22 calculates the bioelectric impedance value of the subject based on the alternating current value and the voltage value (Step S12). The calculated bioelectric impedance value is stored in the storage unit 24 (Step S13).

In this stage, in order to induce a change in body orientation, an indication for instructing the subject to make a bending and stretching exercise is indicated on the display 4. In this embodiment, it instructs the subject to make 10 cycles of bending and stretching exercise (Step S14).

The subject stands up from the seating section 2 and takes the exercises as instructed, and then again sits on the seating section 2 and presses the decision/end switch 5e (Step S15). In this stage, the arithmetic controller 22 again measures the bioelectric impedance (Step S16).

Then the arithmetic controller 22 uses the bioelectric impedance value measured in this step and another bioelectric impedance value having stored in the storage unit 24 at Step S13 to execute an arithmetic operation. In this arithmetic operation, a difference ($\Delta BI$) between the bioelectric impedance values before and after the posture change is calculated by using an equation below, and thus calculated value is compared with a reference value to make a determination based on whether or not that reference value is exceeded.

$$\Delta BI = (BI \text{ value before posture change}) - (BI \text{ value after posture change}) \quad (1)$$

It is to be noted that the reference value is represented by the $\Delta BI$ (reference BI) calculated by those values before and after the posture change of an ordinary healthy person and is different depending on the particular sex and age, and accordingly a plurality of reference values has been stored in the storage unit 24. This is based on the consideration that typically women are more likely to develop the lower limb deep-vein thrombosis as compared to men, and so older persons are. Accordingly, for the female or aged subject, a higher reference value BI is selected and used for the comparison. Further, the reference value BI may be modified in response to the relevance degree of subject to respective factors involved in the lower limb deep-vein thrombosis set at Step S6. Again, the higher reference value BI is selected for the higher relevance degree (Step S17).

Now, using actual figures, a method of determination will be described.

Assuming that the bioelectric impedance values measured between both feet are 500 $\Omega$ and 450 $\Omega$, respectively, before and after the bending and stretching exercises. The reference BI value selected was 30 $\Omega$. Then, using the equation (1), $$\Delta BI = 500 - 450 = 50$$

In this case, the $\Delta BI$ is greater than the reference BI value, and so it is determined that the subject is normal. It is considered that the muscular pumping action caused by the bending and stretching exercises has forced the blood having stored in the lower limb deep-vein to be circulated across the body and associatively the bioelectric impedance value has been dropped. The determination is based on the thinking that such variation in the impedance value should occur in those healthy persons who are considered less possible to develop the lower limb deep-vein thrombosis.

In this embodiment, the case of $\Delta BI$ value equal to or greater than the reference value (30 $\Omega$) is specified as a level 0, indicating a lower probability of the development. The case of $\Delta BI$ value smaller than the reference value (30 $\Omega$) but greater than $\frac{2}{3}$ thereof (20 $\Omega$) is specified as a level 1, the case-of $\Delta BI$ value equal to or smaller than $\frac{2}{3}$ of the reference value BI (20 $\Omega$) but greater than $\frac{1}{3}$ thereof (10 $\Omega$) is specified as a level 2, and the $\Delta BI$ value equal to or smaller than $\frac{1}{3}$ of the reference value (10 $\Omega$) is specified as a level 3. This means the higher level implies the higher probability of the development. As pointed above, since the higher reference BI value may be selected for the female, the aged person and the subject having more relevance factors involved in the lower limb deep-vein thrombosis, this highly set reference value may not be easily exceeded, and accordingly, the determined level and thus the level indicative of the probability of the development should be higher for those subjects in this category even with the same $\Delta BI$ in the measured result.

The display 4 indicates the level representing the determined result (Step S18).

Further, such an advice relating to the method for preventing the development of lower limb deep-vein thrombosis is also indicated (Step S19). This type of advice may include the following contents.

Take in an appropriate amount of water.

Avoid drinking.

Change positions of your legs frequently.

Do stretching and massaging of your legs.

Avoid a tight fitting belt, girdles or stockings, and wear a loose fitting clothes.

Then, the subject can print that determined result and the advice on a sheet of paper. If the print switch 5f is pressed (Step S20), the printer 6 executes the printing operation and ejects the printed sheet of paper (Step S21).

After finishing the printing operation or after a predetermined time period having elapsed in case of no pressing of the print switch 5f, the indication of the display 4 goes out to end the full course of the operation and the power is also turned off.

In the first embodiment of the present invention as discussed above, the determination on the status has been made from the variation of the bioelectric impedance values measured before and after the posture change, but the determination may be given from the bioelectric impedance value measured only once after the posture change. In that case, after a predetermined time of constraint to the lower limb motions followed by the motion which can make effective the muscular pumping action, the bioelectric impedance value is measured, and thus measured value is compared to the reference value representing the corresponding bioelectric impedance value for the ordinary healthy person, thereby enabling the determination.

Turning now to a second embodiment of the present invention, such an apparatus will be described that can provide a determination on the status relating to the deep-vein thrombosis based on a blood transfer and storage capacity induced from the gradient of bioelectric impedance, as previously discussed.

Figure 6:
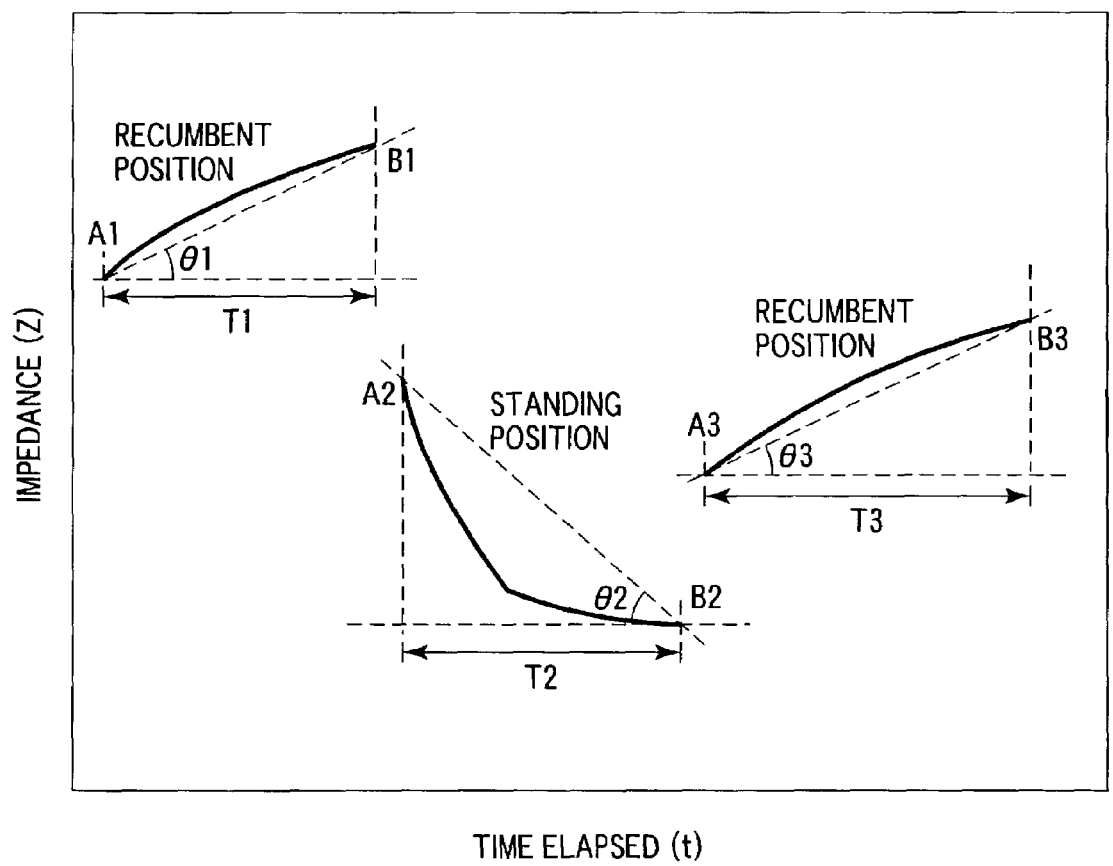
FIG. 6 is a diagram illustrating a measuring principle for a determination apparatus according to a second embodiment of the present invention.

FIG. 6 is a diagram for illustrating a principle of determination by using the variation in the bioelectric impedance value in conjunction with the posture change as shown in FIG. 1.

Assuming that a gradient of bioelectric impedance for the period of the first recumbent position is designated as θ1, an bioelectric impedance value measured at an initial point (A1) of this period as $Z_{A1}$, a bioelectric impedance value measured at an end point (B1) of this period as $Z_{B1}$, and a time required from A1 to B1 as T1, then $$\theta 1 = (Z_{B1} - Z_{A1})/T1 \qquad (2)$$

Similarly, assuming that a gradient of bioelectric impedance for the subsequent period of the standing position is designated as θ2, an bioelectric impedance value measured at an initial point (A2) of this period as $Z_{A2}$, a bioelectric impedance value measured at an end point (B2) of this period as $Z_{B2}$, and a time required from A2 to B2 as T2, then $$\theta 2 \ (Z_{A2} - Z_{B2})/T2 \qquad (3)$$

Similarly, assuming that a gradient of bioelectric impedance for the period of the last recumbent position is designated as θ3, an bioelectric impedance value measured at an initial point (A3) of this period as $Z_{A3}$, a bioelectric impedance value measured at an end point (B3) of this period as $Z_{B3}$, and a time required from A3 to B3 as T3, then $$\theta 3 = (Z_{B3} - Z_{A3})/T3 \qquad (4)$$

Thus determined θ1 and θ3 represent a quantity of body fluid flowing from the lower limbs to the trunk region of the body per unit time, while θ2 represents inversely a quantity of body fluid flowing from the trunk region to the lower limbs per unit time. Those subjects having the higher θ1 and θ3 values can be said to have the status unlikely to allow the body fluid to be stored in the lower limbs, or the status unlikely to allow the blood to be stored therein, while inversely those subject having the higher θ2 can be said to have the status apt to allow the body fluid to be stored in the lower limbs, or the higher possibility to develop the deep-vein thrombosis.

Based on such a principle, in the second embodiment, the bioelectric impedance is measured and a determination is made on the basis of the gradient or the variation degree thereof.

Since the determination apparatus according to the second embodiment may be represented by a schematic perspective view similar to FIG. 2 shown with reference to the first embodiment with an exception that the seating section thereof should be modified to allow the subject to take the recumbent position, and a block diagram thereof maybe also similar to FIG. 3, therefore the drawings specific to this apparatus should be omitted but respective components thereof will be designated by the same reference numerals as those in the first embodiment in the description.

Figure 7:
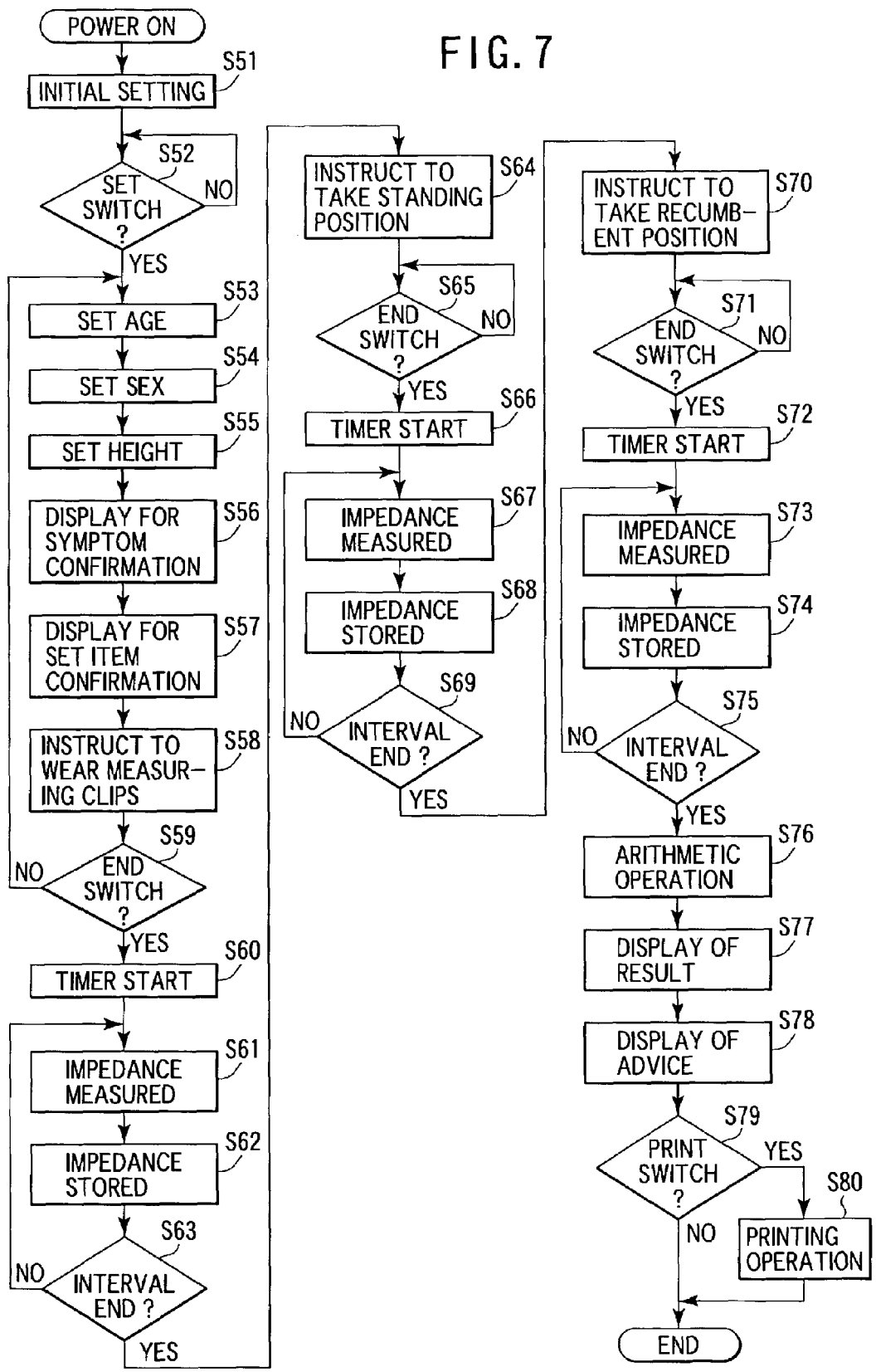
FIG. 7 is an operation flow chart for the determination apparatus according to the second embodiment of the present invention.

FIG. 7 is a chart showing a flow of operation in the second embodiment of the present invention. Since the operation from Step S51 to Step S58 is same as the operation from Step S1 to Step S8 in the first embodiment, therefore the explanation therefor should be herein omitted.

The subject after finishing the fitting of the measuring clips 7a, 7b presses the decision/end switch 5e (Step S59).

In response thereto, the display 4 indicates "Stay at rest in a recumbent position with your legs unmoved." and the clock 25 is activated to start clocking a predetermined time period. In this embodiment, the clock clocks for five minutes (Step S60). After that, the apparatus starts to measure a bioelectric impedance of the subject (Step S61). A calculated bioelectric impedance value is stored in the storage unit 24 (Step S62).

Then, it is checked whether or not the five-minute-period has elapsed (Step S63), and if not, the process returns to Step S61 to continue the measuring of the bioelectric impedance. Since the body orientation of the subject has been changed from the standing or sitting position to the recumbent position, the body fluid having stored in the lower limbs may move into the trunk region of the body during this period. Owing to this, the bioelectric impedance value measured between both feet may rise gradually as represented by a curve shown in the left-hand side of FIG. 1. This is based on the fact that the blood contains much electrolyte, such as natrium ion (Na+) and kalium ion (K+), and so has a highly conductive property, and if the quantity of blood is decreased, then consequently the impedance value in that region should rise-up.

At Step S63, if the five-minute-interval has elapsed, then an indication to instruct the subject to stand up is made appeared on the display 4 (Step S64). In response to this, the subject brings himself/herself into the standing position and presses the decision/end switch 5e (Step S65).

Then, the display 4 indicates the instruction "Keep standing on the spot with your legs unmoved." and the clock 25 is activated again to start clocking for another certain time period. The clock 25 at this time clocks for five minutes (Step S66). After that, the apparatus starts to measure the bioelectric impedance of the subject (Step S67). The calculated bioelectric impedance value is stored in the storage unit 24 (Step S68).

Then, it is checked whether or not the five-minute-interval has elapsed (Step S69), and if not, the process returns to Step S67 to continue the measuring of the bioelectric impedance. Since the body orientation of the subject has been changed from the recumbent position into the standing position, the body fluid, including the blood that has been circulating entirely within the body, will begin to be stored in the lower limbs. Owing to this, the bioelectric impedance value measured between both feet is gradually lowered as represented by the curve shown in the middle section of FIG. 1. Initially, the bioelectric impedance drops rapidly and then it shows a gradual decrease as the quantity of the blood in the lower limbs approaching to the limit of the storage capacity.

If the five-minute-interval has elapsed at Step S69, an indication to instruct the subject to lay himself/herself down is shown on the display 4 (Step S70). In response thereto, the subject brings himself/herself into the recumbent position and presses the decision/end switch 5e (Step S71).

Then, the display 4 indicates the instruction "Stay at rest in the recumbent position with your legs unmoved." and the clock 25 is activated to start clocking for another certain time period. The clock 25 at this time clocks for five minutes (Step S72). After that, the apparatus starts to measure the bioelectric impedance of the subject (Step S73). The calculated bioelectric impedance value is stored in the storage unit 24 (Step S74).

Then, it is checked whether or not the five-minute-interval has elapsed (Step S75), and if not, the process returns to Step S74 to continue the measuring of the bioelectric impedance. Since the body orientation of the subject has been changed from the standing position to the recumbent position, the body fluid, including the blood that has been stored in the lower limbs, may begin to move again into the trunk region. Owing to this, the bioelectric impedance value measured between both feet rises gradually as represented by the curve shown in the right-hand side of FIG. 1.

If the five-minute-interval has elapsed at Step S75, the measurement of the bioelectric impedance comes to end, and an arithmetic operation will begin (Step S76).

In this arithmetic operation, the gradient of bioelectric impedance represented by the variation thereof per unit time is determined for each period of particular body orientation. The θ1, θ2 and θ3 may be calculated from the bioelectric impedance values, each measured at the initial moment in each period of particular body orientation ($Z_{A1}$, $Z_{A2}$, $Z_{A3}$) as well as the bioelectric impedance values, each measured at the last moment in each period ($Z_{B1}$, $Z_{B2}$, $Z_{B3}$) and the measuring times (T1, T2, T3), by using the above equations (2)–(4).

Thus calculated θ1, θ2 and θ3 are compared to respectively corresponding reference values stored in the storage unit 24, thereby determining whether or not the subject has the status apt to develop the deep-vein thrombosis. For the purpose of the present invention, the term, respectively corresponding reference values, refers to the gradients of bioelectric impedance represented by the variations thereof per unit time for ordinary healthy person in respective periods of particular body orientations. These reference values, similarly to those in the first embodiment, can be modified in dependence on the sex, the age or the relevance degree of subject to the factors involved in the lower limb deep-vein thrombosis and accordingly the storage unit 24 has stored a plurality of reference values for each period of particular body orientation.

If thus calculated θ1 or θ3 is lower than their reference value and the θ2 is greater than its reference value, which indicates a larger storage capacity in the lower limbs, then it can be said that the subject has the status apt to develop the deep-vein thrombosis. Accordingly, the comparisons of the gradients of three impedances are conducted to see whether or not the θ1 and θ3 have fallen on or lower than the reference values and whether or not the θ2 has fallen on or higher than the reference value and it is determined how much the conditions are satisfied, wherein in the case of all three conditions being satisfied, then it is specified as a level 0, in the case of one of the conditions unsatisfied, then as a level 1, in the case of two of the conditions unsatisfied, as a level 2, and in the case of all three conditions unsatisfied, as a level 3.

The display 4 indicates the level representing the determined result (Step S77).

Further, an advice relating to the method for preventing the development of lower limb deep-vein thrombosis is also indicated (Step S78). This advice may include those previously presented with reference to the first embodiment and so will be omitted herein.

Then, the subject can print that determined result and the advice on a sheet of paper. If the print switch 5f is pressed (Step S79), the printer 6 executes the printing operation and ejects the printed sheet of paper (Step S80).

After finishing the printing operation or after a predetermined time period having elapsed in case of no pressing of the print switch 5f, the indication of the display 4 goes out to end the full course of the operation and the power is also turned off.

Some of the preferred embodiments of the present invention have been described as above, but the reference value of the bioelectric impedance (reference BI) shown in the description of the first embodiment has been used by way of example only and the reference BI can be appropriately modified corresponding to, in addition to the sex and age, a set of personal physical information such as a body fat ratio or a BMI (Body-mass Index). This is based on the fact that a fatted subject having relatively larger fat mass is typically considered to have a smaller muscle mass and inevitably have a poorer ability to make effective the muscular pumping action.

Further, although in the illustrated embodiments, the reference value has been described to be stored in the storage unit in a mode consisting of a plurality of values, a similar effect can be obtained even in an alternative mode of the reference value, in which one reference value may be stored so as to be modified in response to the entered personal physical information, thereby providing a determination, or otherwise, instead of modifying the reference value, a measured value of the bioelectric impedance may be corrected in response to the personal physical information and the corrected bioelectric impedance value is compared to the reference value, thereby providing a determination on the status.

Further, although the period for constraining the motions of legs before the measurement has been set as a five-minute-interval in the above illustrated embodiments, the constraint period may be made longer so that more blood may be stored in the lower limbs, which enables more accurate determination on whether or not the subject has the status apt to develop the deep-vein thrombosis in the lower limb region. However, it is also no good for the body of subject that any real thrombus is adversely produced by a long time constraining of the legs, and so an adequate time period should be set by taking exhaustion or pain of the subject as well as convenience into consideration.

Further, although in the above illustrated embodiment, such a configuration has been employed in which the measuring clip is equipped with the electrode to be attached on the ankle region as a means for measuring the bioelectric impedance, an adhesive electrode may be used which may be affixed directly onto the skin in the vicinity of the ankle region, or an alternative configuration may be employed in which an electrode may be arranged on a surface of the measuring unit on which a foot of a subject is to be placed so that a sole of foot may come in contact therewith, thereby allowing for the measurement of the bioelectric impedance.

Further, although in the above illustrated embodiment, the bioelectric impedance has been measured between one and the other feet, such an impedance can be measured by utilizing only a single leg to determine whether or not he/she has the status apt to develop the deep-vein thrombosis. In such a case, it will be possible to make such a decision by, for example, attaching electrodes to the ankle region and the knee or thigh of a single leg to measure the bioelectric impedance between them.

Further, although the status of the subject likely to develop the lower limb deep-vein thrombosis is indicated by levels as the determined result in the above embodiments, the indication of the determined result is not limited to this but may be represented by % or with terms, such as "Normal", "Be careful" or "Caution needed".

Further, from the viewpoint that the stand-by time until the execution of the bioelectric impedance measurement before the posture change in the first embodiment as well as the time period of recumbent position in the second embodiment are considered burdensome to the subject, if employing such a configuration that allows an index concerning to a body constitution such as the body fat ratio or the body water content, which can be calculated from the bioelectric impedance value, to be calculated and indicated to the subject during the above time period, then the apparatus may be more convenient such that the subject would be no more particularly sensitive to the waiting time.

Further, if the determination based on the difference between the bioelectric impedance values measured respectively before and after a posture change as shown in the first embodiment is combined with the determination based on the gradient of bioelectric impedance for a period of a certain body orientation as shown in the second embodiment so as to provide the apparatus allowing for the determination by using two indexes, then a more accurate determination can be provided on whether or not the subject has the status apt to develop the deep-vein thrombosis.

EFFECT OF THE INVENTION

With the deep-vein thrombosis determination apparatus of the present invention, which has been configured so as to determine whether or not a subject has the status apt to develop deep-vein thrombosis in the lower limb region, the subject can recognize his/her status in a simple manner.

Further, since the deep-vein thrombosis determination apparatus of the present invention can measure the bioelectric impedance values before and after a posture change and then determine from the variation thereof whether or not a subject has the status apt to develop the deep-vein thrombosis, therefore this determination can be given at the time of a real event of blood transfer produced by the muscular pumping action of the subject, which may directly affect the development of the thrombus, and accordingly the determination can be more accurate.

Further, since the deep-vein thrombosis determination apparatus of the present invention can determine the gradient of bioelectric impedance represented by a variation thereof per unit time after a subject having changed his/her body orientation, for example, from a recumbent position into a standing position, and then determine based on the value of gradient whether or not the subject has the status apt to develop the deep-vein thrombosis, therefore the determination can be based on a blood storage capacity in the lower limb region and accordingly, the determination whether or not the subject has the status apt to develop the lower limb deep-vein thrombosis can be more accurate.

Further, since the deep-vein thrombosis determination apparatus of the present invention can select a reference value suitable for determination based on the personal physical information for a subject, therefore a more accurate determination can be provided on whether or not the subject has the status apt to develop the lower limb deep-vein thrombosis.

Still further, since the deep-vein thrombosis determination apparatus of the present invention can modify the reference value to be used for the determination based on the relevance degree of the subject to the factors considered to be involved in the lower limb deep-vein thrombosis, therefore a more accurate determination can be provided on whether or not the subject has the status apt to develop the lower limb deep-vein thrombosis.

Yet further, since the deep-vein thrombosis determination apparatus of the present invention can provide the advice relating to a method for preventing the development of the lower limb deep-vein thrombosis, therefore the subject can obtain knowledge of a prevention method and can avoid the development of the disease.

It is believed that if the deep-vein thrombosis determination apparatus of the present invention is provided in a lobby of an airport thus to arrange a condition allowing an expected passenger for an airplane to have a measurement before boarding, then the passenger can have an idea beforehand on whether or not he/she has the status apt to develop the lower limb deep-vein thrombosis and the passenger can be also provided with the information on the method for preventing the development of the disease, which may help prevent the development of the disease during and after the flight.

What is claimed is:

1. A deep-vein thrombosis determination apparatus comprising a plurality of electrodes, a current supply unit, a voltage measuring unit, an arithmetic operation unit, a storage unit, a determination unit and an informing unit, wherein said plurality of electrodes includes current supply electrodes and voltage measuring electrodes to be installed in contact with both feet of a subject's body;

said current supply unit supplies an alternating current between said current supply electrodes;

said voltage measuring unit measures a voltage between said voltage measuring electrodes;

said arithmetic operation unit uses said plurality of electrodes, said current supply unit and said voltage measuring unit to execute an arithmetic operation on the bioelectric impedance value at least two times, one before and one after a change in a subject's body orientation, and to execute an arithmetic operation on a variation of the measured bioelectric impedance values;

said storage unit stores a reference value;

said determination unit determines whether or not the subject has a constitution apt to develop the deep-vein thrombosis in a region of lower limb based on a comparison between the calculated variation of the bioelectric impedance value and the reference value stored in the storage unit; and said informing unit informs the subject of a determined result and provides an advice relating to a method for preventing the development of the deep-vein thrombosis in a region of lower limb;

said apparatus further comprising an input device, wherein said input device is used to input a relevance degree of subject to respective factors involved in a deep-vein thrombosis in a region of lower limb; and said determination unit modifies the reference value to be used in a determination based on the input relevance degree of subject.

2. A deep-vein thrombosis determination apparatus comprising a plurality of electrodes, a current supply unit, a voltage measuring unit, an arithmetic operation unit, a storage unit, a determination unit and an informing unit, wherein said plurality of electrodes includes current supply electrodes and voltage measuring electrodes to be installed in contact with both feet of a subject's body;

said current supply unit supplies an alternating current between said current supply electrodes;

said voltage measuring unit measures a voltage between said voltage measuring electrodes;

said arithmetic operation unit calculates a bioelectrical impedance value from the supplied alternating current and the measured voltage and executes an arithmetic operation on a gradient of bioelectrical impedance represented by a variation thereof per unit time from a time period for which a subject remains in a certain body orientation and a variation of the bioelectrical impedance value during said time period of that certain body orientation;

said storage unit stores a reference value;

said determination unit determines whether or not the subject has a constitution apt to develop the deep-vein thrombosis in a region of lower limb based on a comparison between the calculated gradient of bioelectric impedance represented by the variation thereof per unit time and the reference value stored in the storage unit; and said informing unit informs the subject of a determined result and provides an advice relating to a method for preventing the development of the deep-vein thrombosis in a region of lower limb;

said apparatus further comprising an input device, wherein said input device is used to input a relevance degree of subject to respective factors involved in a deep-vein thrombosis in a region of lower limb; and said determination unit modifies the reference value to be used in a determination based on the input relevance degree of subject.

3. A deep-vein thrombosis determination apparatus comprising a plurality of electrodes, a current supply unit, a voltage measuring unit, an arithmetic operation unit, a storage unit, a determination unit and an informing unit, wherein said plurality of electrodes includes current supply electrodes and voltage measuring electrodes to be installed in contact with both feet of a subject's body;

said current supply unit supplies an alternating current between said current supply electrodes;

said voltage measuring unit measures a voltage between said voltage measuring electrodes;

said arithmetic operation unit uses said plurality of electrodes, said current supply unit and said voltage measuring unit to execute an arithmetic operation on the bioelectric impedance value at least two times, one before and one after a change in a subject's body orientation, and to execute an arithmetic operation on a variation of the measured bioelectric impedance values;

said storage unit stores a reference value;

said determination unit determines whether or not the subject has a constitution apt to develop the deep-vein thrombosis in a region of lower limb based on a comparison between the calculated variation of the bioelectric impedance value and the reference value stored in the storage unit; and said informing unit informs the subject of a determined result and provides an advice relating to a method for preventing the development of the deep-vein thrombosis in a region of lower limb;

said apparatus further comprising an input device, wherein said input device is used to input personal information relating to a physical body of a subject;

said storage unit stores a plurality of reference values each corresponding to a different set of said personal information; and said determination unit selects a certain reference value among those reference values stored in the storage unit to be used in a determination based on said input set of physical information of the subject.

4. A deep-vein thrombosis determination apparatus comprising a plurality of electrodes, a current supply unit, a voltage measuring unit, an arithmetic operation unit, a storage unit, a determination unit and an informing unit, wherein said plurality of electrodes includes current supply electrodes and voltage measuring electrodes to be installed in contact with both feet of a subject's body;

said current supply unit supplies an alternating current between said current supply electrodes;

said voltage measuring unit measures a voltage between said voltage measuring electrodes;

said arithmetic operation unit calculates a bioelectrical impedance value from the supplied alternating current and the measured voltage and executes an arithmetic operation on a gradient of bioelectrical impedance represented by a variation thereof per unit time from a time period for which a subject remains in a certain body orientation and a variation of the bioelectrical impedance value during said time period of that certain body orientation;

said storage unit stores a reference value;

said determination unit determines whether or not the subject has a constitution apt to develop the deep-vein thrombosis in a region of lower limb based on a comparison between the calculated gradient of bioelectric impedance represented by the variation thereof per unit time and the reference value stored in the storage unit; and said informing unit informs the subject of a determined result and provides an advice relating to a method for preventing the development of the deep-vein thrombosis in a region of lower limb;

said apparatus further comprising an input device, wherein said input device is used to input personal information relating to a physical body of a subject;

said storage unit stores a plurality of reference values each corresponding to a different set of said personal information; and said determination unit selects a certain reference value among those reference values stored in the storage unit to be used in a determination based on said input set of physical information of the subject.

* * * * *